US006686999B2

(12) United States Patent
Ketkar

(10) Patent No.: US 6,686,999 B2
(45) Date of Patent: Feb. 3, 2004

(54) METHOD OF USING AN AEROSOL TO CALIBRATE SPECTROMETERS

(75) Inventor: Suhas Narayan Ketkar, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 110 days.

(21) Appl. No.: 10/020,559

(22) Filed: Dec. 14, 2001

(65) Prior Publication Data

US 2003/0112431 A1 Jun. 19, 2003

(51) Int. Cl.[7] .............................. G01J 3/30; G01J 3/42; G01N 21/31; G01N 33/20; G01D 18/00
(52) U.S. Cl. .................... 356/316; 356/945; 250/252.1; 250/288; 250/339.07; 250/339.08; 250/339.09; 250/341.5; 436/73

(58) Field of Search ................................ 356/316, 319, 356/945; 250/252.1, 288, 339.07, 339.08, 339.09, 341.5; 436/73

(56) References Cited

U.S. PATENT DOCUMENTS 5,792,663 A * 8/1998 Fry et al.
5,866,899 A * 2/1999 Hossain
6,043,486 A * 3/2000 Hossain
6,437,325 B1 * 8/2002 Reilly et al.

OTHER PUBLICATIONS

"Investigations into the Direct Analysis of Semiconductor . . . ", Hutton, et al, J. Anal. At. Spectrometry, 1990.
"Determination of Organometallic Compounds by Capillary . . . ", Kim, et al, J. of High Resol. Chroma., 1992.
"Automated Sampling System for Direct Determination . . . " Baaske & Telgheder, J. Anal. At. Spectrum, 1995.

* cited by examiner

*Primary Examiner*—Frank G. Font
*Assistant Examiner*—Khaled Brown
(74) *Attorney, Agent, or Firm*—Geoffrey L. Chase

(57) ABSTRACT

Using a nebulizer gas, sub micron and micron size particulates can be generated from a solution containing salts covering a broad range of elements. The fractional concentration of elements can be determined by bubbling the aerosol through aqueous acid and analyzing the aqueous acid for metals. The nebulizer can be coupled to an ICP (Inductively Coupled Plasma) torch and the ICPMS (Inductively Coupled Plasma Mass Spectrometer) or ICPOES (Inductively Coupled Plasma Optical Emission Spectrometer) response to different elements can be determined. This provides the response factor of the ICPMS or ICPOES for different elements.

19 Claims, 5 Drawing Sheets

METHOD OF USING AN AEROSOL TO CALIBRATE SPECTROMETERS

BACKGROUND OF THE INVENTION

The present invention relates to a method of calibrating a mass spectrometer that analyzes elemental impurities in a gas stream. More particularly, the present invention is concerned with using a dry aerosol for calibrating an inductively coupled plasma mass spectrometer (ICPMS) or an inductively coupled plasma optical emission spectrometer (ICPOES).

In general, an ICPMS or an ICPOES uses an inductively coupled plasma source to dissociate the sample into its constituent atoms or ions, exciting them to a level where they emit light of a characteristic wavelength. In ICPOES, a detector measures the intensity of the emitted radiation and calculates the concentration of that particular element in the sample, whereas in ICPMS a detector measures the mass to charge ratio of the ion of that particular element and calculates the concentration of that particular element in the sample.

In principle, gases can be analyzed using ICPMS or ICPOES; however, in actuality, one can obtain only qualitative information about the gases since there are very few gas phase metal standards available. The current method for determining metallic contamination in gases is to obtain a sample in an aqueous form and analyze the aqueous solutions for metals. This is necessitated by the fact that it is easy to calibrate analytical instruments like an inductively coupled plasma mass spectrometer (ICPMS) or an inductively coupled plasma optical emission spectrometer (ICPOES), etc., using standards in an aqueous form.

In particular, the procedure currently employed by the industry consists of trapping the metallic impurities from the sample gas into an aqueous medium (e.g., hydrolyzing the gas, if the gas is hydrolyzable, or bubbling the gas through an aqueous acid to trap the metallic impurities). In most cases, the aqueous sample that is obtained undergoes a laborious sample preparation step whereby the metallic impurities trapped in the aqueous samples are transferred (using evaporation and reconstitution) to a dilute nitric acid solution. The resulting aqueous nitric acid is analyzed using either an ICPMS or an ICPOES. The sampling and sample preparation step can easily take upwards of 8 hours. The analysis is a fairly complicated process and at each step of the sampling and sample preparation there is ample opportunity for contamination which can lead to results that are higher than the actual metallic content in the sample gas. This is particularly true for elements like Na, K, Ca and Zn which are abundant in the ambient environment. Unfortunately, these elements, particularly Na and K, are critical impurities for the semiconductor industry since the presence of these elements on the layers being deposited can lead to device failures.

Ideally, one would like to introduce the gas sample directly into the analytical instrument to obtain the metallic content but, at the present time, there is no method for such a direct analysis. In particular, there have been attempts in the past to directly analyze gases using both ICPMS as well as ICPOES. Unfortunately, in all of these attempts it was recognized that calibration of the instrument is a major challenge. It was recognized that very few elemental standards can be obtained in the gas phase. In the earlier reported experiments, standards of As (as Arsine), Phosphorous (as Phosphine), Si (as Silane), Fe and Ni (as their carbonyls) and I from methyl iodide, etc. (see "Investigations into the Direct Analysis of Semiconductor Grade Gases by Inductively Coupled Plasma Mass Spectrometery," by Hutton et al., J. Anal. At. Spectrometry, Vol. 5; 1990) were used to calibrate the ICPMS. These attempts were successful because there are compounds of these elements which are gases; thus, these gases can be mixed with an inert gas (e.g., nitrogen) to form standards. This can be, in principle, extended to other elements as long as stable gas phase compounds of the other elements are available. However, a vast majority of elements, which are of concern to the semiconductor industry, are not available as gas phase compounds and no attempt was made to calibrate other elements of interest. Moreover, it was recognized that the gaseous standards used were highly toxic (including the compounds of As, P, Ni and Fe) and were a major safety concern. Consequently, most of these experiments were performed in laboratories and were able to demonstrate that gaseous samples can be directly analyzed using an ICPMS or ICPOES. Due to the issue with calibration of the ICPMS for a majority of elements that are of interest, this practice has not been carried out as a routine analytical method.

Other references related to this type of analysis are "Determination of Organometallic Compounds by Capillary Gas Chromotography-Inductively Coupled Plasma Mass Spectrometry", by Kim et al., J. of High Resolution Chromatography, Vol. 15; p. 665; 1992; and "Automated Sampling System for the Direct Determination of Trace Amounts of Heavy Metals in Gaseous Hydrogen Chloride by Atomic Absorption Spectrometry" by Baaske & Telgheder, J. Anal. At. Spectrum, Vol. 10; p. 1077; 1995.

Thus, there remains a need for a method of calibrating an ICPMS or an ICPOES for analyzing impurities in directly-injected gases.

BRIEF SUMMARY OF THE INVENTION

A method for calibrating an inductively-coupled plasma (ICP) spectrometer (e.g., an ICP mass spectrometer or an ICP optical emission spectrometer) to analyze metallic impurities in gases. The method comprises the steps of: (a) providing a sample gas having unknown metallic impurities therein; (b) nebulizing the sample gas with a first aqueous standard (e.g., deionized water) containing no metallic impurities into an aerosol and wherein the nebulizing comprises a known efficiency; (c) inputting and analyzing the aerosol in the ICP spectrometer to measure intensities of metallic impurities therein and wherein the analyzing comprises the application of the known efficiency to the measured intensities to form a first set of metallic impurities data; (d) conducting a standard addition process utilizing different aqueous standards of increasing concentrations of metallic impurities therein that are nebulized with the sample gas and analyzed in the ICP spectrometer to obtain a plurality of sets of data for each of the metallic impurities and to which the known efficiency is applied; (e) deriving a relationship between measured intensity and concentration for each of said metallic impurities (e.g., a calibration curve) based upon the plurality of sets of data and the first set of metallic impurities data and wherein the linear relationship defines a slope and a measured intensity intercept; and (f) determining the concentration of metallic impurities in the sample gas from the absolute value of the measured intensity intercept divided by the slope for each of the linear relationships.

A system for use in calibrating an inductively-coupled plasma (ICP) spectrometer (e.g., an ICP mass spectrometer or an ICP optical emission spectrometer) to analyze metallic impurities in gases. The system comprises: at least three different aqueous standards; a nebulizer (e.g., a microflow or a microconcentric nebulizer) for nebulizing each one of the at least three different aqueous standards in series with a sample gas having unknown metallic impurities therein to form an aerosol and wherein the nebulizer has a known efficiency; an ICP spectrometer for receiving and analyzing the intensities of metallic impurities in the aerosol to generate data regarding intensities of metallic impurities; and means for deriving a linear relationship between intensity and concentration for each of the metallic impurities based upon the data, wherein the linear relationship defines a slope and an intensity intercept, and wherein the deriving means also determines the concentration of metallic impurities in the sample gas from the absolute value of the intensity intercept divided by the slope for each of the linear relationships and wherein the deriving means takes into account the known efficiency of the nebulizer.

A system for use in calibrating an inductively-coupled plasma (ICP) spectrometer (e.g., an ICP mass spectrometer or an ICP optical emission spectrometer) to analyze metallic impurities in gases. The system comprises: at least three different aqueous standards; a nebulizer (e.g., a microflow or a microconcentric nebulizer) for nebulizing each one of the at least three different aqueous standards in series with a sample gas having unknown metallic impurities therein to form a wet aerosol; a desolvator (e.g., a membrane desolvator), coupled to the nebulizer, for converting the wet aerosol into a dry aerosol and wherein said nebulizer and desolvator have a known efficiency; an ICP spectrometer for receiving and analyzing the intensities of metallic impurities in the dry aerosol to generate data regarding intensities of metallic impurities; and means for deriving a linear relationship between intensity and concentration for each of the metallic impurities based upon the data, wherein the linear relationship defines a slope and an intensity intercept, and wherein the deriving means also determines the concentration of metallic impurities in the sample gas from the absolute value of the intensity intercept divided by the slope for each of the linear relationships and wherein the deriving means takes into account the known efficiency of the nebulizer and the desolvator.

BRIEF DESCRIPTION OF SEVERAL VIEWS OF THE DRAWINGS

The invention will be described by way of example with reference to the accompanying drawings, in which.

DETAILED DESCRIPTION OF THE INVENTION

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

As will be discussed in detail below, the invention of the present application facilitates the direct connection of a sample gas cylinder to the ICPMS or ICPOES instrument which greatly reduces the total analysis time, as well as minimizes the possibility of contamination. Furthermore, as will also be discussed below, the invention surpasses conventional gas analysis methods using ICPMS or ICPOES which provide only qualitative information about metallic impurities.

Figure 1:
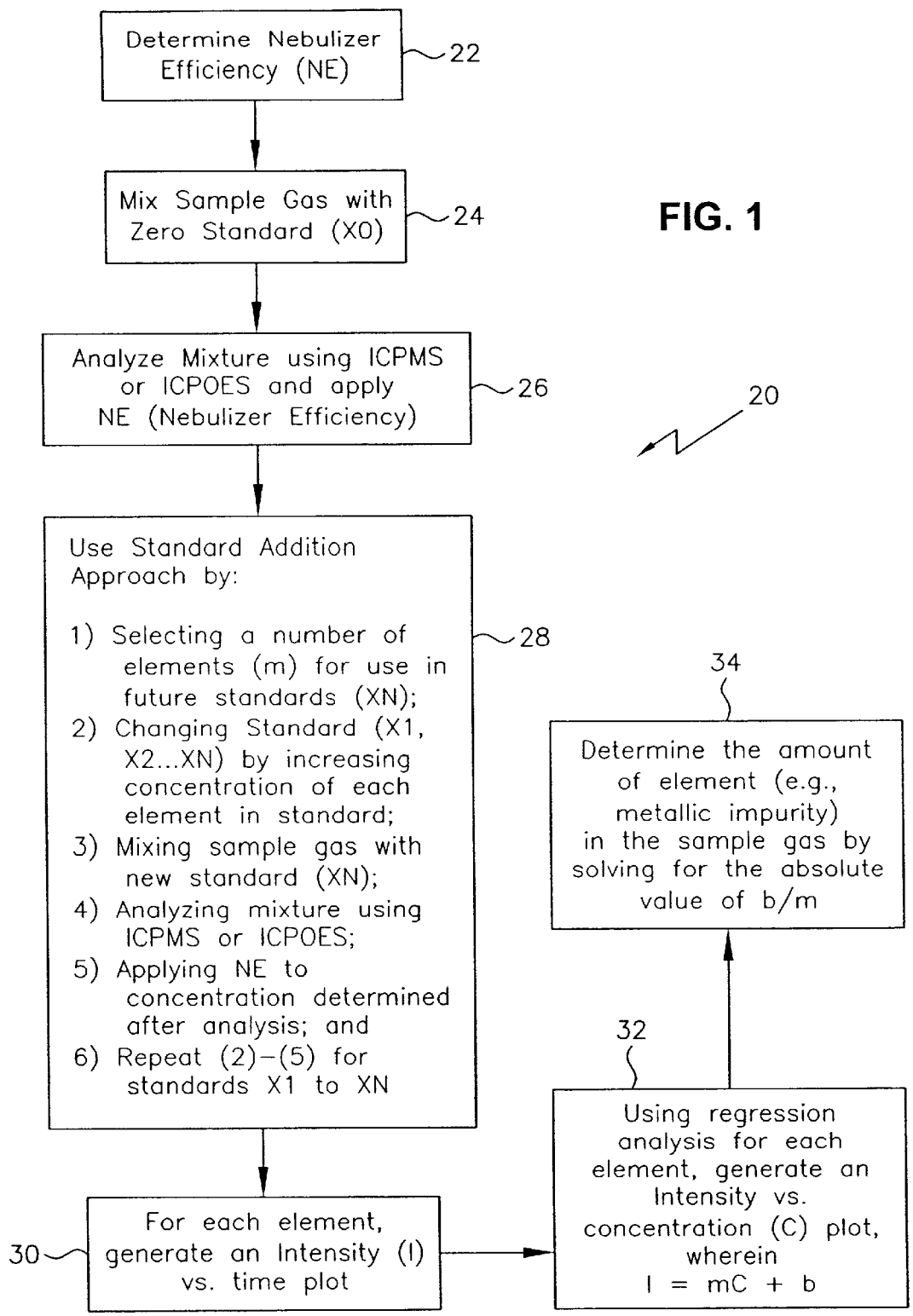
FIG. 1 is a block diagram of the method of the present invention.

FIG. 1 depicts the method 20 of the present invention which permits the determination of the type and amount of an unknown element (i.e., metallic impurity) in a sample gas. However, before discussing the method, it is necessary to discuss the system used in carrying out the method 20.

Figure 2:
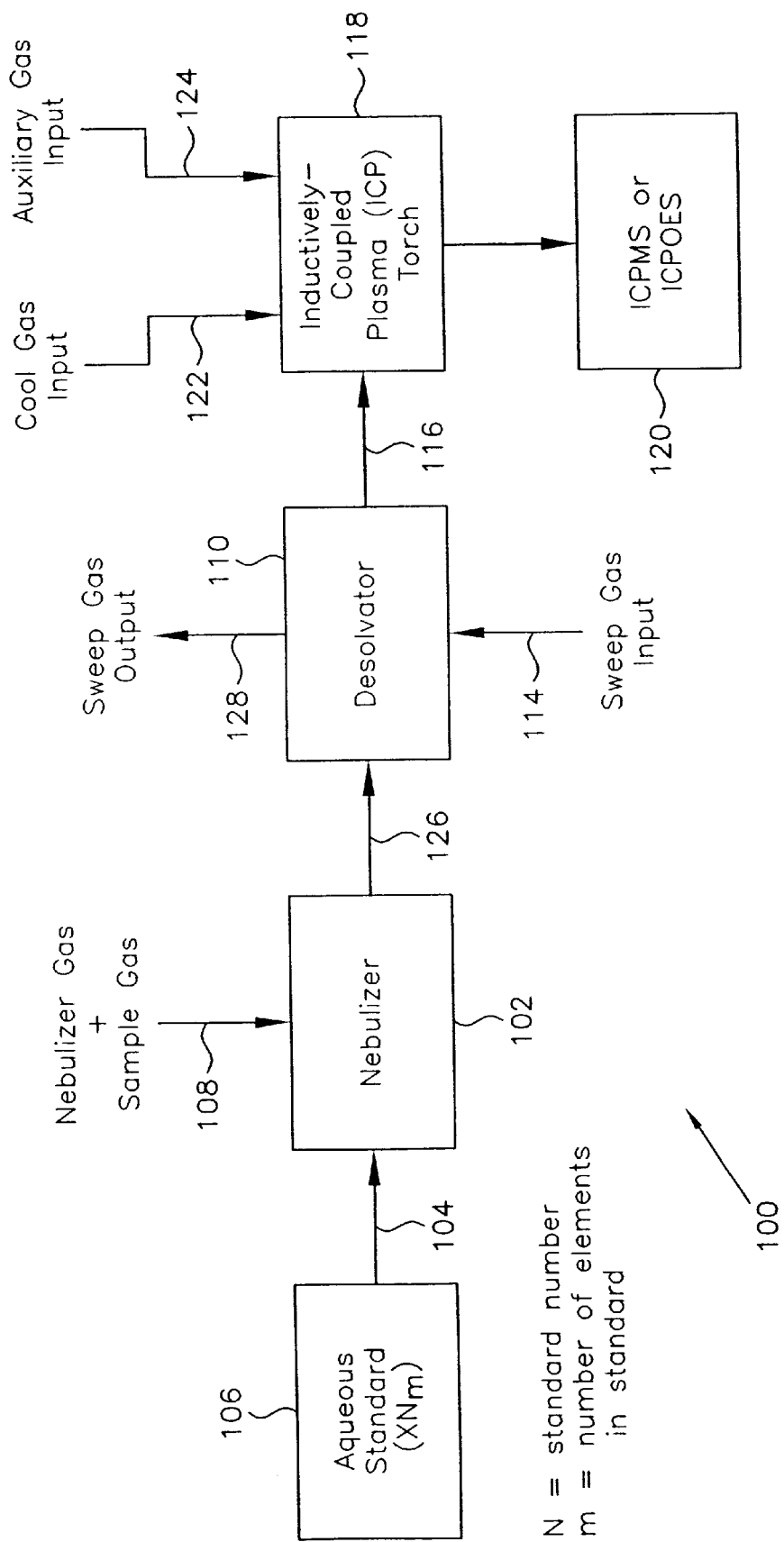
FIG. 2 is a block diagram of a system for carrying out the method of the present invention.

As shown in FIG. 2, the system 100 uses a low flow nebulizer 102 (e.g., a microflow or a microconcentric nebulizer) that receives a liquid 104 from an aqueous standard 106 ($XN_m$, where "X" indicates "standard", "N" is the number of the standard, and "m" indicates the number of elements or, for purposes of this application, metallic impurities). In general, aqueous standards 106 are elemental standards that have been dissolved in an aqueous medium. Typically, nitrate salts of different elements are dissolved in nitric acid. By choosing the amount of salt and the amount of nitric acid, aqueous solutions containing different concentrations of elements can be generated. For example, a single element standard of K at a concentration of 10 ppm can be made as follows: dissolving 10 $\mu$g of a potassium salt in 1 cc of nitric acid. Alternatively, a 10 ppm multi-element standard can be obtained by dissolving 10 $\mu$g each of the salts of different desired elements and then dissolving that in 1 cc of nitric acid.

Figure 3:
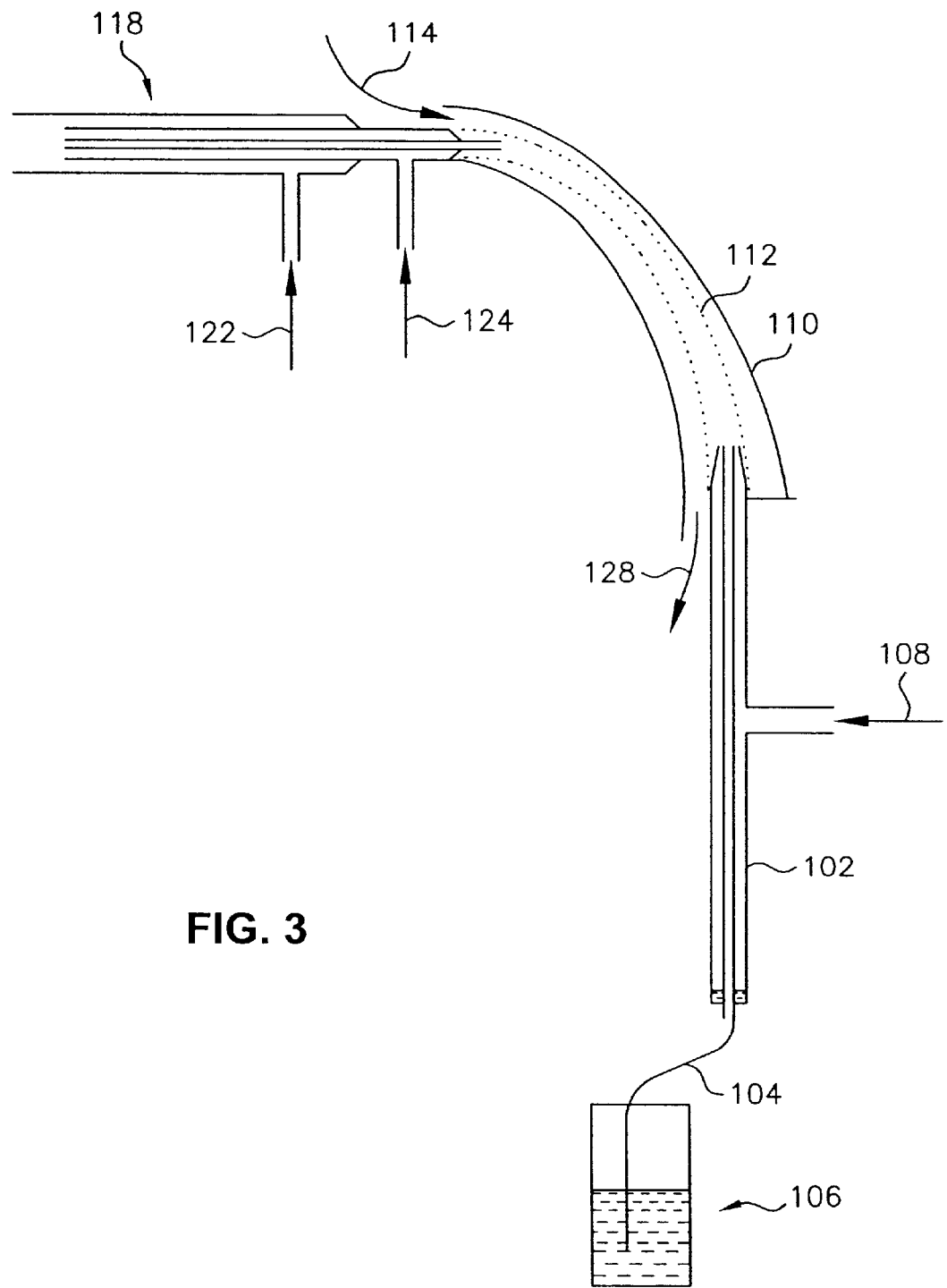
FIG. 3 is a functional diagram of a portion of the system of FIG. 2.

A combination 108 of a nebulizer gas (e.g., Argon) and the sample gas (i.e., the gas under test which contains an unknown metallic impurity) are injected into the nebulizer 102. The output of the nebulizer 102 is coupled to a desolvator 110 having a membrane 112 (e.g. Teflon®, Nafion®, etc., see FIG. 3) which also receives a sweep gas (e.g., nitrogen or any inert gas) input 114. The desolvator 110 reduces water loading from the aqueous standard 106 and generates a dry aerosol. This dry aerosol is mixed with the sample gas and this combination 116 is introduced into the torch 118 of the ICPMS or ICPOES instrument 120. A cool gas (e.g., argon) input 122 and an auxiliary gas (e.g., argon) input 124 are also provided to the ICP torch 118. Typically, ICPMS and ICPOES techniques rely on generating an argon Inductively-Coupled Plasma (ICP). This argon plasma facilitates the excitation and ionization of the trace metallic impurities that can be subsequently analyzed by a MS (mass spectrometer) or OES (Optical Emission Spectrometer).

In particular, the nebulizer 102 is used to make an aerosol from the aqueous standard 106. The aqueous standard 106 contains a known concentration of a multi-element (m) standard (X). Argon is used as the nebulizer gas and to this nebulizer gas a known amount of the gas to be analyzed (i.e., sample gas) is added. The wet aerosol 126 of the aqueous standard 106 is then carried by the mixture of argon and the sample gas into the desolvator 110. The desolvator 110 consists of a semi-permeable membrane 112 (FIG. 3) fabricated from materials such as Teflon®, Nafion®, etc. Although not shown, the desolvator 110 is housed in an enclosure which can be heated. In the desolvator 110, the solvent evaporates, thereby producing solute particles mixed in the solvent vapors. The solute particles comprise the atoms of the metallic salt impurities that are dissolved in the aqueous standard 106. These particles, when transported to the plasma of the ICPMS are atomized and ionized and are then detected by the instrument 120, which permits instrument 120 response to a particular element (e.g., intensity/concentration, as will be discussed below), thereby calibrating the instrument 120. The membrane 112 is chosen such that solvent vapors permeate through the membrane 112 and are carried away by the use of a countercurrent flow output 128 of a dry sweep gas.

The dry solute particles are carried away by the mix of argon and the sample gas into the plasma torch 118 of an ICP instrument 120. The RF (radio frequency) plasma generated in the torch breaks apart the solute particles and excites and ionizes the constituent elements of the particles which can be subsequently detected by an OES or MS.

Figure 4:
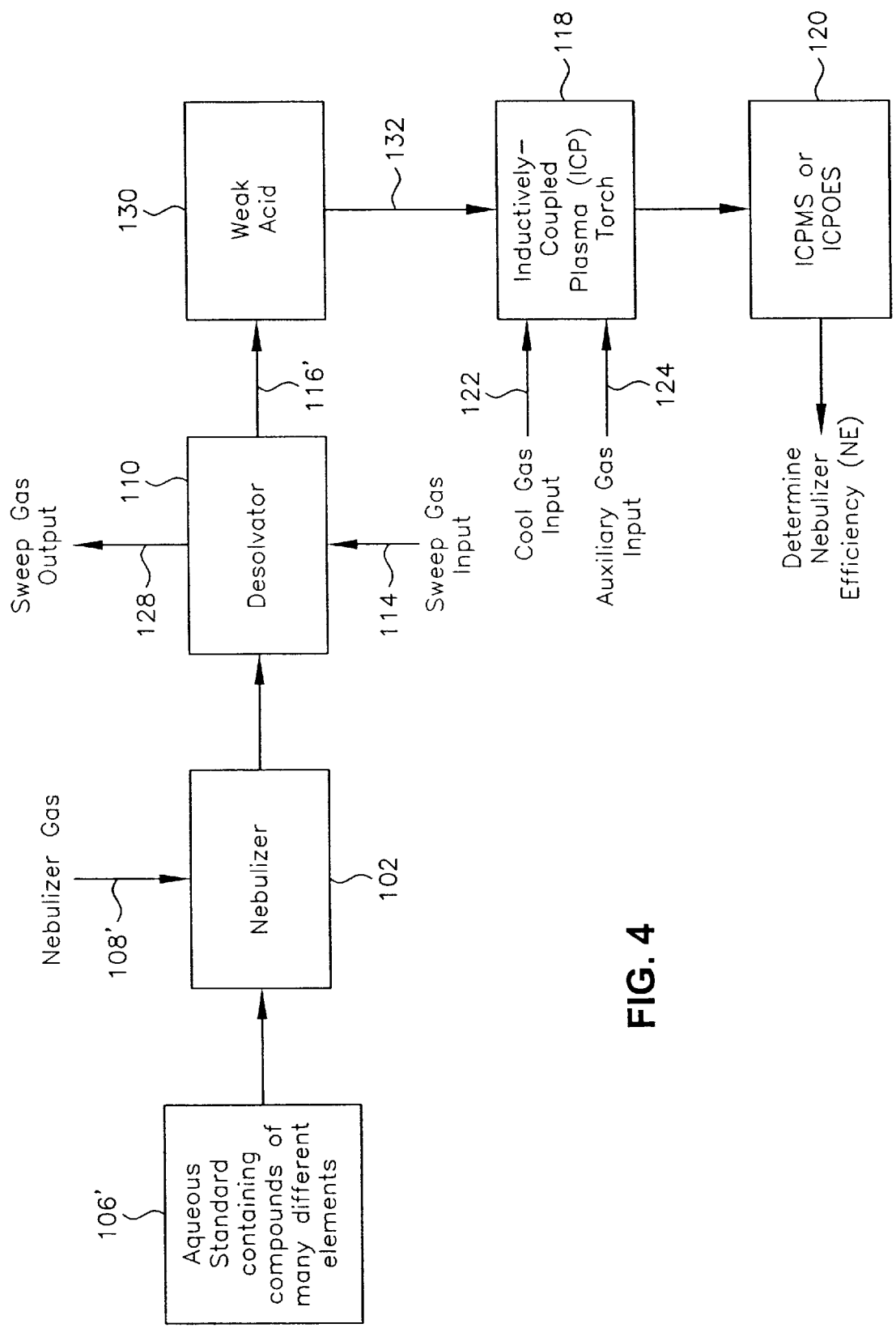
FIG. 4 is a block diagram of the system used for determining the nebulizer efficiency.

In order to calibrate the instrument 120 the efficiency of the nebulizer 102 has to be determined, i.e., the amount of a given element present in the output 116 being generated. This can be accomplished by dissolving the dry aerosol in a weak acid (e.g., 2% nitric acid, although higher concentrations, up to 70%, can also be used, etc.) and using conventional techniques to quantify the amount. In particular, as shown in FIG. 4, to determine the nebulizer efficiency (NE), an aerosol is generated from an aqueous standard 106' which contains compounds of many different elements. The nebulizer gas input 108' (the sample gas is not used in the NE determination) is provided to the nebulizer 102 and the wet aerosol 126' is then fed to the desolvator 110. The dry aerosol 116' is then dissolved in a weak acid 130 (typically 2%–10% nitric acid, although any acid is sufficient; the choice of the acid is governed by the desire to dissolve all the compounds). The result is an aqueous sample 132 (i.e., elemental impurities in the acid) which is fed to the ICP torch 118 and an analyzed through the instrument 120. The instrument 120 analysis reveals the actual concentration of the known compounds in the aqueous sample 132 as compared to the known concentration in the aqueous standard 106'. As a result, the nebulizer 102 efficiency can then be determined. It should be noted that the efficiency of the nebulizer 102 is a one-time determination and need only be re-calculated whenever it or the desolvator 110 are changed.

Once the nebulizer 102 efficiency is known, the analysis of the sample gas is conducted in accordance with the method 20, as shown in FIG. 1.

In particular, the nebulizer 102 efficiency (NE) is first determined in step 22. Next, in step 24, the sample gas is mixed with the zero standard, 0X, i.e., the gas is sampled with a standard with "zero" concentration of the elements to be analyzed (deionized (DI) water, which has very low levels of metallic impurities, or a 2% ultrapure nitric acid) being nebulized. In step 26, the ICPMS or ICPOES measures the intensity corresponding to different elements. Intensities measured for a given element correspond to the amount of that element in the sample gas and the aqueous standard 106. The instrument 120 response is measured over a time "t". This procedure is repeated a number of times to obtain adequate number of repeats.

The instrument 120 is calibrated using a standard addition approach, step 28. The concept of the standard addition approach is to use several aqueous standards of increasing concentrations of a predetermined number of elements (e.g., metals) that are mixed with the sample gas and then analyzed in the instrument 120. Depending upon the need, the ICPMS or ICPOES analysis can be restricted to a list of desired elements, although, in principle, the measured intensity for all elements can be measured.

Figure 5:
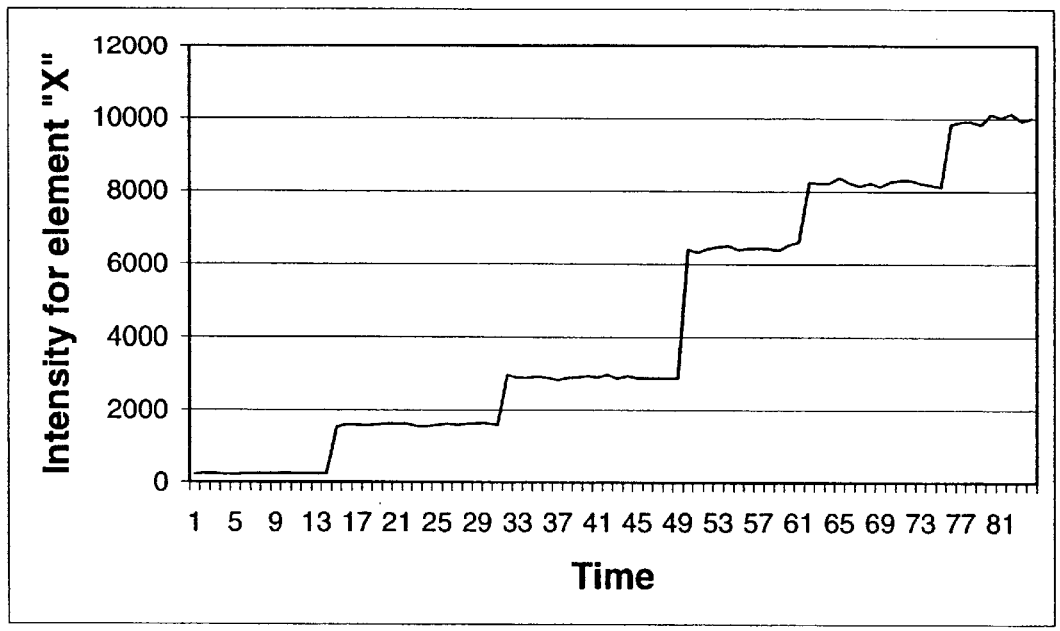
FIG. 5 is a response/time graph depicting the measured intensity vs. time for a particular element.

After obtaining a large number of data points of varying concentrations of different elements in the mixture via the ICPMS or ICPOES analyses, in step 30, an intensity vs. time plot for each element measured is generated. As shown in FIG. 5, this response/unit time is generated based on the instrument 120 response and has the appearance of a staircase, with each stair corresponding to a different concentration, as the standards were changed. This plot depicts what occurs if the concentration were to be increased after each interval of time t. Examples of computer applications that can generate such plots from such measured data are Excel by Microsoft®, Sigmaplot® by SPSS Inc., Origin by OriginLab® Corporation, etc.

Figure 6:
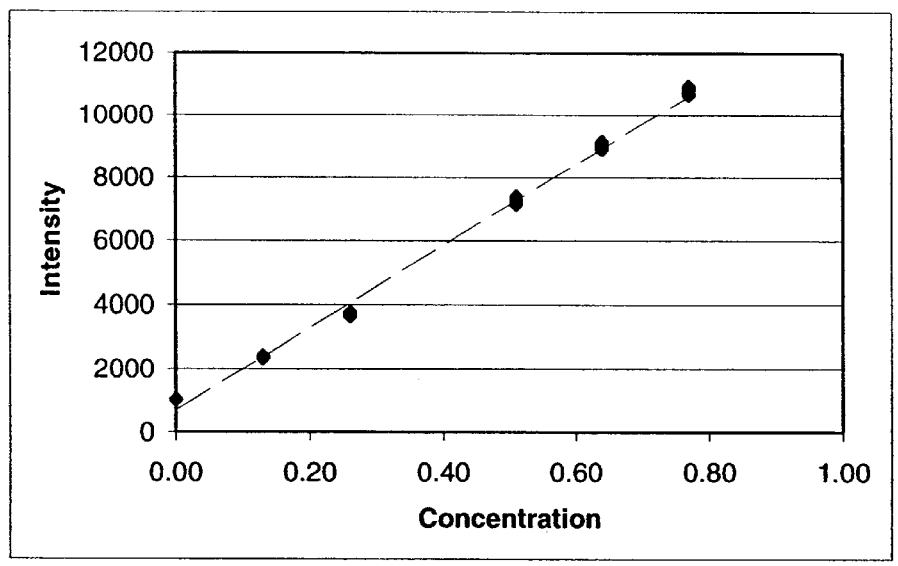
FIG. 6 is a calibration curve for the measured intensity of vs. concentration of a particular element.

Next, in step 32, a linear representation or plot of the concentration of each element, in an intensity vs. concentration plane, can be derived from the data of step 30. In particular, as shown in FIG. 6, a calibration curve is then constructed to represent response/unit time vs. the concentration of a particular element in the sample gas. To construct such a curve, a regression analysis (curve fitting) method is used to relate the measured intensity to the concentration. Since the ICPMS or ICPOES technique is very linear, a linear least squares fitting may be used. Depending upon the nature of the generated data either an ordinary least squares or a weighted least squares approach can be used. Thus, using the relationship, $$I=mC+b,$$

where
I is the intensity;
m is the slope;
C is the concentration; and
b is the intensity-axis intercept,
the values for m and b are obtained from the plot and the concentration of a particular element at zero intensity (I=0), which corresponds to the zero standard (0X), is given by $$\left|\frac{b}{m}\right|.$$

Since the contribution to the presence of a particular element in the instrument 120 is from either the sample gas or the zero standard, and since the zero standard contains no added elements, this calculated concentration corresponds to the concentration of the metallic impurity in the sample gas. A calibration curve for each of the selected elements is constructed in a similar fashion and the concentration corresponding to zero standard is calculated. Examples of computer applications that can generate such calibration curves are Excel by Microsoft®, Sigmaplot® by SPSS Inc., Origin by OriginLab® Corporation, etc.

It should be noted that although it is typical to run five to six standards, i.e., $5X_i$–$6X_i$, a minimum of three is usually necessary, i.e., 0X, $1X_i$ and $2X_i$.

It should be further noted that although the preferred embodiment of the present invention utilizes a dry aerosol for calibrating ICPMS or ICPOES, a wet aerosol can also be utilized. Thus, it is within the broadest scope of this invention to omit the use of the membrane desolvator 110. Although the sensitivity of the present invention which includes the membrane desolvator 110 is better than the present invention which omits the membrane desolvator 110, the overall operation of the present invention is still the same. Correspondingly, where the membrane desolvator 110 is omitted, the calculation of the nebulizer efficiency (NE) does not include any desolvating process efficiency.

What is claimed is:

1. A method for calibrating an inductively-coupled plasma (ICP) spectrometer to analyze metallic impurities in gases, said method comprising the steps of:

(a) providing a sample gas having unknown metallic impurities therein;

(b) nebulizing the sample gas with a first aqueous standard containing no metallic impurities into an aerosol, said nebulizing comprising a known efficiency;

(c) inputting and analyzing said aerosol in the ICP spectrometer to measure intensities of metallic impurities therein, said analyzing comprising the application of said known efficiency to said measured intensities to form a first set of metallic impurities data;

(d) conducting a standard addition process utilizing different aqueous standards of increasing concentrations of metallic impurities therein that are nebulized with the sample gas and analyzed in said ICP spectrometer to obtain a plurality of sets of data for each of said metallic impurities and to which said known efficiency is applied;

(e) deriving a relationship between measured intensity and concentration for each of said metallic impurities based upon said plurality of sets of data and said first set of metallic impurities data, said relationship defining a slope and a measured intensity intercept; and (f) determining the concentration of metallic impurities in the sample gas from the absolute value of said measured intensity intercept divided by said slope for each of said linear relationships.

2. The method of claim 1 wherein said ICP spectrometer is an ICP mass spectrometer.

3. The method of claim 1 wherein said ICP spectrometer is an ICP optical emission spectrometer.

4. The method of claim 1 wherein said standard addition process utilizes at least two different aqueous standards.

5. The method of claim 1 wherein said known efficiency of said step of nebulizing is obtained by:

(a) providing a test aqueous standard containing known concentrations of compounds;

(b) nebulizing said test aqueous standard with a nebulizer gas to form a test aerosol;

(c) mixing said test aerosol with a weak acid to form an aqueous sample;

(d) inputting and analyzing said aqueous sample into said ICP to determine actual concentrations of said compounds in said test aerosol; and (e) comparing said actual concentrations with said known concentrations to derive said efficiency.

6. The method of claim 1 wherein said step of conducting a standard addition process comprises:

(a) providing a new aqueous standard containing known concentrations of metallic impurities therein;

(b) nebulizing the sample gas with said new aqueous standard into another aerosol;

(c) inputting and analyzing said another aerosol in the ICP spectrometer to measure intensities of metallic impurities therein, said analyzing comprising the application of said known efficiency to said measured intensities to form a portion of said plurality of sets of data for each of said metallic impurities and to which said known efficiency is applied;

(d) repeating steps (a)–(c) using increasing known concentrations of metallic impurities therein.

7. The method of claim 1 wherein said step of nebulizing the sample gas with a first aqueous standard yields a wet aerosol and also comprises desolvating said wet aerosol into a dry aerosol and wherein said nebulizing and desolvating comprise said known efficiency.

8. The method of claim 7 wherein said known efficiency of said steps of nebulizing and desolvating is obtained by:

(a) providing a test aqueous standard containing known concentrations of compounds;

(b) nebulizing and desolvating said test aqueous standard with a nebulizer gas to form a test dry aerosol;

(c) mixing said test dry aerosol with a weak acid to form an aqueous sample;

(d) inputting and analyzing said aqueous sample into said ICP to determine actual concentrations of said compounds in said test dry aerosol; and (e) comparing said actual concentrations with said known concentrations to derive said efficiency.

9. The method of claim 7 wherein said step of conducting a standard addition process comprises:

(a) providing a new aqueous standard containing known concentrations of metallic impurities therein;

(b) nebulizing the sample gas with said new aqueous standard into another wet aerosol and desolvating said another wet aerosol into another dry aerosol;

(c) inputting and analyzing said another dry aerosol in the ICP spectrometer to measure intensities of metallic impurities therein, said analyzing comprising the application of said known efficiency to said measured intensities to form a portion of said plurality of sets of data for each of said metallic impurities and to which said known efficiency is applied;

(d) repeating steps (a)–(c) using increasing known concentrations of metallic impurities therein.

10. A system for use in calibrating an inductively-coupled plasma (ICP) spectrometer to analyze metallic impurities in gases, said system comprising:

at least three different aqueous standards;

a nebulizer for nebulizing each one of said at least three different aqueous standards in series with a sample gas having unknown metallic impurities therein to form an aerosol, said nebulizer having a known efficiency;

an ICP spectrometer for receiving and analyzing the intensities of metallic impurities in said aerosol to generate data regarding intensities of metallic impurities; and means for deriving a linear relationship between intensity and concentration for each of said metallic impurities based upon said data, said linear relationship defining a slope and an intensity intercept, said deriving means also determining the concentration of metallic impurities in the sample gas from the absolute value of said intensity intercept divided by said slope for each of said linear relationships, and wherein said deriving means takes into account said known efficiency of said nebulizer.

11. The system of claim 10 wherein one of said at least three different aqueous standards comprises deionized water that contains no metallic impurities.

12. The system of claim 11 wherein the other two of said at least three different aqueous standards comprises solutions containing at least one metallic impurity and wherein each of said other two aqueous solutions comprise different concentrations of said at least one metallic impurity.

13. The system of claim 10 wherein said ICP spectrometer is an ICP mass spectrometer.

14. The system of claim 10 wherein said ICP spectrometer is an ICP optical emission spectrometer.

15. A system for use in calibrating an inductively-coupled plasma (ICP) spectrometer to analyze metallic impurities in gases, said system comprising:

at least three different aqueous standards;

a nebulizer for nebulizing each one of said at least three different aqueous standards in series with a sample gas having unknown metallic impurities therein to form a wet aerosol;

a desolvator, coupled to said nebulizer, for converting said wet aerosol into a dry aerosol and wherein said nebulizer and desolvator have a known efficiency;

an ICP spectrometer for receiving and analyzing the intensities of metallic impurities in said dry aerosol to generate data regarding intensities of metallic impurities; and means for deriving a linear relationship between intensity and concentration for each of said metallic impurities based upon said data, said linear relationship defining a slope and an intensity intercept, said deriving means also determining the concentration of metallic impurities in the sample gas from the absolute value of said intensity intercept divided by said slope for each of said linear relationships, and wherein said deriving means takes into account said known efficiency of said nebulizer and desolvator.

16. The system of claim 15 wherein one of said at least three different aqueous standards comprises deionized water that contains no metallic impurities.

17. The system of claim 16 wherein the other two of said at least three different aqueous standards comprises solutions containing at least one metallic impurity and wherein each of said other two aqueous solutions comprise different concentrations of said at least one metallic impurity.

18. The system of claim 15 wherein said ICP spectrometer is an ICP mass spectrometer.

19. The system of claim 15 wherein said ICP spectrometer is an ICP optical emission spectrometer.

* * * * *